(12) United States Patent
Nagy

(10) Patent No.: US 8,137,916 B2
(45) Date of Patent: *Mar. 20, 2012

(54) SUSCEPTIBILITY GENE FOR ALZHEIMER'S DISEASE

(75) Inventor: Zsuzsanna Nagy, Birmingham (GB)

(73) Assignee: Isis Innovation Ltd., Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/912,421

(22) Filed: Oct. 26, 2010

(65) Prior Publication Data

US 2011/0045486 A1 Feb. 24, 2011

Related U.S. Application Data

(63) Continuation of application No. 10/557,948, filed as application No. PCT/GB2004/002222 on May 21, 2004, now Pat. No. 7,842,455.

(30) Foreign Application Priority Data

May 22, 2003 (GB) .................................. 0311835.3

(51) Int. Cl.
   - *C12Q 1/68* (2006.01)
   - *C07H 21/02* (2006.01)
   - *C07H 21/04* (2006.01)

(52) U.S. Cl. ...................... 435/6.11; 536/23.1; 536/24.3

(58) Field of Classification Search ........................ None
See application file for complete search history.

(56) References Cited

U.S. PATENT DOCUMENTS

| 2004/0132113 A1 | 7/2004 | Nagy |
| 2007/0072184 A1 | 3/2007 | Nagy |

FOREIGN PATENT DOCUMENTS

| WO | WO 02/073212 | 9/2002 |
| WO | WO 2004/104226 | 12/2004 |

OTHER PUBLICATIONS

Langdahl, Bente et al. Osteoporotic fractures are assoicated with an 86 base pair repeat polymoprhism in the interleukin 1 receptor antagonist gene but not with polymoprhisms in the interleukin 1B gene. 2000. Journal of Bone and Mineral Research. vol15 No. 3 pp. 402-414.*

Wall, Jeffery et al. Haplotype blocks and linkage disequilbirium in the human genome. 2003. Nature Reviews Genetics. vol. 4 pp. 587-597.*

Facher, Evan et al. Assoication between human cancer and two polymorphisms occurring together in the p21 cyclin dependent kinsase inhibitor gene. Cancer 1997 vol. 79 No. 12 pp. 2424-2429.*

Syvanen, Ann Christine. Accessng genetic variation: genotyping single nucleotide polymorphisms. 2001 Nature Reviews Genetics vol. 2 pp. 930-942.*

Blacker, et al. (2003) *"Results of a High-Resolution Genome Screen of 437 Alzheimer's Disease Families,"* Human Molecular Genetics, 12(1):23-32.

Facher, E.A., et al. (1997) *"Association Between Human Cancer and Two Polymorphisms Occurring Together in the p21Waf1/Cip1 Cyclin-Dependent Kinase Inhibitor Gene,"* Cancer 79(12):2424-2429.

Goodman, et al. (2003) *"Evidence for Defective Retinoid Transport and Function in Late AD Onset Alzheimer's Disease,"* Proc. Natl. Acad. Sci. (U.S.A.) 100(5):2901-2905.

Harima, Y., et al. (2001) *"Polymorphism of the WAF1 Gene Is Related to Susceptibility to Cervical Cancer in Japanese Women,"* Int. J. Mol. Med. 7(3):261-264 (Abstract Only).

Langdahl et al. (2000) *"Osteoporotic fractures are associated with an 86 base pair repeat polymoprhism in the interleukin 1 receptor antagonist gene but not with polymoprhisms in the interleukin 1 B gene,"* J. Bone Mineral Research 15(3):402-414.

Nagy, Z. et al. (1998) *"The Cell Division Cycle and the Pathophysiology of Alzheimer's Disease,"* Neuroscience 84(4):731-739.

Nagy, Z. (2000) *"Cell Cycle Regulatory Failure in Neurones: Causes and Consequences,"* Neurobiology of Aging 21(6):761-769.

Nagy, Z., et al. (2003) *"Cell Cycle Kinesis in Lymphocytes in the Diagnosis of Alzheimer's Disease,"* Neurosci. Lett. 317(2):81-84.

Wall, J. et al. (2003) *"Haplotype Blocks and Linkage Disequilbirium in the Human Genome,"* Nature Reviews Genetics 4:587-597.

Li, G. et al. (2005) *"Genetic Polymorphisms of P21 Are Associated With Risk of Squamous Cell Carcinoma of the Head and Neck"* Carcinogenesis 26(9):1596-1602.

p21 Polymorphisms (NCBI http://www.ncbi.nlm.nih.gov/sites/entrez); 2011; pp. 1-52.

* cited by examiner

*Primary Examiner* — Amanda Shaw

(74) *Attorney, Agent, or Firm* — Jeffrey I. Auerbach; The Auerbach Law Firm, LLC

(57) ABSTRACT

The invention relates to genetic screens for susceptibility to Alzheimer's disease. In particular, the invention provides genetic screens based on genotyping of the p21E2c31 C/A polymorphism and/or the p21E3+20 C/T polymorphism in the p21cip 1 gene.

14 Claims, 3 Drawing Sheets

Men

Pearson's R p=0.02

Women

Non significant

Men

Pearson's R p=0.014

Women

Non significant

SUSCEPTIBILITY GENE FOR ALZHEIMER'S DISEASE

CROSS-REFERENCE TO RELATED APPLICATIONS

This application claims priority to United States Patent Application Serial No. PCT/GB2004/00222 (filed May 21, 2004; lapsed) and Ser. No. 10/557,948 (filed Sep. 11, 2006; pending), both of which applications are herein incorporated by reference in their entireties.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

1. Field of the Invention

The present invention relates to genetic screens for susceptibility to Alzheimer's disease. In particular, the invention relates to genetic screens based on genotyping of the p21E2c31 polymorphism and/or the p21E3+ 20 C/T polymorphism in the p21cip 1 gene.

2. Description of Related Art

As life expectancy increases, Alzheimer's disease (AD) is becoming a major health problem in the western world. There has been intensive research aimed at identifying a reliable cure or preventive measures for the disease, so far without success.

It is becoming widely accepted that cell cycle re-entry and subsequent regulatory failure in neurons is at the pathogenic basis of Alzheimer's disease (Nagy, Z., M. M. Esiri, and A. D. Smith, The cell division cycle and the pathophysiology of Alzheimer's disease. Neuroscience, 1998. 84(4): p. 731-739; also applicant's published International patent application WO 02/073212). There are also indications that this regulatory dysfunction of the cell division cycle is not restricted to the neurons of Alzheimer's disease patients (Nagy, Z., et al., Cell cycle kinesis in lymphocytes in the diagnosis of Alzheimer's disease. Neurosci Lett, 2002. 317(2): p. 81-4). There is evidence that other cell types, such as lymphocytes and fibroblasts, originating from Alzheimer's disease sufferers have deficient cell cycle regulatory machinery. This regulatory deficiency leads to aberrant response of these cells to various in vitro stimuli (see WO 02/073212). Furthermore, Alzheimer's disease patients are more prone to certain types of cancers than the age matched control subjects. On the basis of this evidence, it is plausible that the regulatory failure on the G1/S transition point responsible for the development of AD-related pathology in neurons is due to mutations or allelic variations of the cell cycle regulatory genes, particularly the cyclin-dependent kinase inhibitors or CDKIs.

Since cell cycle disturbances seem to be a very early event in Alzheimer's disease, preceding the development of any clinical symptoms, the identification of mutations and polymorphisms in cell cycle regulatory genes will allow the identification of patients who do not have fully developed Alzheimer's disease but may be at increased risk of developing the disease. This may in turn allow early intervention with strategies aimed at preventing the development and/or delaying the onset of Alzheimer's disease pathology.

The human cyclin-dependent kinase inhibitor-1A gene (OMIM accession number 116899, referred to herein as p21cip 1, OMIT nomenclature CDKN1A, also known in the art as CDK-interacting protein 1, CIP1, p21, wildtype p53-activated fragment 1, or WAF1) is one of the CDKI genes responsible for the regulation of the G1/S transition point. The gene encodes a 21-kd protein that is found in immunoprecipitates of cyclin A, cyclin D1, cyclin E, and CDK2. The p21cip 1 gene has been mapped to 6p21.2 by fluorescence in situ hybridization.

A polymorphism has been identified at codon 31 of p21cip 1 (Chedid, M. et al., Oncogene, Vol 9(10), 3021-4, 1994), where a single point mutation changes the normal or "wildtype" allele AGC (ser) to a variant allele AGA (arg). The OMIM accession number for this polymorphism (referred to herein as p21E2c31) is 116899.0001. The single nucleotide substitution results in the loss of a restriction site and gain of another, allowing for rapid screening of the polymorphism (Chedid, M. et al., 1994, ibid). Analysis of the polymorphism has revealed that it is related to an increased risk of certain types of cancer (Harima, Y., et al., Polymorphism of the WAF1 gene is related to susceptibility to cervical cancer in Japanese women. Int J Mol Med. 2001. 7(3): p. 261-4). A further single nucleotide polymorphism in the p21 gene, a C to T transition occurring 20 nucleotides downstream of the 3' end of exon 3 (referred to herein as p21E3+20 C/T) is also known to be associated with cancer (Facher, E. A., et al., Association between human cancer and two polymorphisms occurring together in the p21Waf1/Cip1 cyclin-dependent kinase inhibitor gene. Cancer, 1997. 79(12): p. 2424-9).

The present inventor has now demonstrated that the p21E2c31 polymorphism shows a significant association with Alzheimer's disease. Furthermore, co-occurrence of the p21E2c31 polymorphism with the p21E3+ 20 C/T polymorphism improves the significance of the association with Alzheimer's disease. These observations have led to the development of novel genetic screens which may be used to identify individuals genetically predisposed to developing Alzheimer's disease.

DESCRIPTION OF THE INVENTION

In accordance with a first aspect of the invention there is provided a method of screening a human subject for pre-disposition to Alzheimer's disease, which comprises genotyping the subject for the p21E2c31 polymorphism in the p21cip 1 gene and/or the p21E3+20 C/T polymorphism in the p21 cip 1 gene, wherein the presence of at least one variant allele p21E2c31 A and/or p21E3+20 T is taken as an indication that the subject is pre-disposed to Alzheimer's disease.

The invention further provides a method for use in diagnosis of Alzheimer's disease in a human subject, which comprises genotyping the subject for the p21E2c31 polymorphism in the p21cip 1 gene and/or the p21E3+20 C/T polymorphism in the p21cip 1 gene, wherein the presence of at least one variant allele p21E2c31 A and/or p21E3+20 T is taken as an indication that the subject has Alzheimer's disease.

The invention still further provides a method of determining any genetic basis for Alzheimer's disease in a human subject, which comprises genotyping the subject for the p21E2c31 polymorphism in the p21cip 1 gene and/or the p21E3+20 C/T polymorphism in the p21cip 1 gene, wherein the presence of at least one variant allele p21E2C31 A and/or p21E3+20 T indicates that this genetic variation contributes to the genetic basis for Alzheimer's disease in the subject.

The methods of the invention are genetic screens which comprise genotyping human subjects for the p21E2c31 polymorphism and/or the p21E3+ 20 C/T polymorphism in the p21cip 1 gene. Subjects having one or two variant alleles (i.e. heterozygotes or homozygotes for the variant allele) at one or both of these loci (the variant alleles being p21E2c31 "A" and p21 E3+20 "T") may be scored, depending on whether the screen is used diagnostically or prognostically, as having a pre-disposition to Alzheimer's disease (AD) or having AD itself.

The term "p21E2c31 polymorphisms refers to a single nucleotide polymorphism in exon 2 of the human p21cip 1 gene. In the context of this application the term "p21E2C31 polymorphism" may be used to refer to the polymorphic locus. The genetic variation is a single nucleotide substitution C→A occurring in codon 31 of the gene (AGC→AGA), resulting in a single amino acid substitution serine(S)→arginine(R) at position 31 in the p21 protein. As aforesaid, this polymorphism is known in the art to be associated with cancer (Chedid et al., Facher et al., ibid). The variant allele of this polymorphism is p21E2c31 A.

The term "p21E3+20 C/T polymorphism" refers to a single nucleotide polymorphism, a single nucleotide substitution C→T, occurring 20 nucleotides downstream of the 3' end of exon 3 of the human p21 cip 1 gene. In the context of this application the term "p21E3+20 C/T polymorphism" may be used to refer to the polymorphic locus. This polymorphism is also known in the art to be associated with cancer (Chedid et al., Facher et al., ibid). The variant allele of this polymorphism is p21E3+20 T.

As illustrated in the accompanying Examples, the inventor has shown that the presence of the variant p21E2c31 "A" allele is significantly associated with increased risk of developing Alzheimer's disease in male subjects and with a reduction in age of onset of Alzheimer's disease in female subjects, as compared to individuals homozygous for the normal allele p21E2c31 "C". The significance of these associations is increased when the p21E2c31 "A" allele occurs together with the p21 E3+20 "T" allele.

The invention also contemplates genetic screens for susceptibility to Alzheimer's disease (AD) based on genotyping of polymorphic variants (whether or not within the p21 cip 1 gene) which have not themselves been shown to be associated with susceptibility to AD in a population-based study, but which are either in linkage disequilibrium with or in close physical proximity to the p21E2c31 polymorphism and/or the p21 E3+ 20 C/T polymorphism. Screens based on genotyping of polymorphic variants in linkage disequilibrium with the p21E2c31 polymorphism and/or the p21E3+20 polymorphism may be used either alone or in conjunction with genotyping of the p21E2c31 polymorphism and/or the p21E3+20 polymorphism.

Therefore, in a further aspect the invention also provides a method of screening a human subject for pre-disposition to Alzheimer's disease, which comprises genotyping the subject for one or more polymorphisms in linkage disequilibrium with the p21E2c31 polymorphism in the p21cip 1 gene and/or one or more polymorphisms in linkage disequilibrium with the p21E3+20 C/T polymorphism in the p21 cip 1 gene, wherein the presence of at least one allele in linkage with the variant allele p21E2c31 A and/or the presence of at least one allele in linkage with the variant allele p21E3+20 T is taken as an indication that the subject is pre-disposed to Alzheimer's disease.

The invention further provides a method for use in diagnosis of Alzheimer's disease in a human subject which comprises genotyping the subject for one or more polymorphisms in linkage disequilibrium with the p21E2c31 polymorphism in the p21cip 1 gene and/or one or more polymorphisms in linkage disequilibrium with the p21E3+20 C/T polymorphism in the p21 cip 1 gene, wherein the presence of at least one allele in linkage with the variant allele p21E2c31 A and/or the presence of at least one allele in linkage with the variant allele p21E3+20 T is taken as an indication that the subject has Alzheimer's disease.

The invention still further provides a method of determining any genetic basis for Alzheimer's disease in a human subject which comprises genotyping the subject for one or more polymorphisms in linkage disequilibrium with the p21E2c31 polymorphism in the p21cip 1 gene and/or one or more polymorphisms in linkage disequilibrium with the p21E3+20 C/T polymorphism in the p21cip 1 gene, wherein the presence of at least one allele in linkage with the variant allele p21E2c31 A and/or the presence of at least one allele in linkage with the variant allele p21E3+20 T indicates that this genetic variation contributes to the genetic basis for Alzheimer's disease in the subject.

In the above methods a positive screening result is indicated by the presence of at least one allele in linkage with p21E2c31 "A" allele and/or at least one allele in linkage with the p21E3+20 "T" allele.

As would be readily apparent to persons skilled in the art of human genetics, "linkage disequilibrium" occurs between a marker polymorphism (e.g. a DNA polymorphism which is "silent") and a functional polymorphism (i.e. genetic variation which affects phenotype or which contributes to a genetically determined trait) if the marker is situated in close proximity to the functional polymorphism. Due to the close physical proximity, many generations may be required for alleles of the marker polymorphism and the functional polymorphism to be separated by recombination. As a result the alleles will be present together on the same haplotype at higher frequency than expected, even in very distantly related people, and are referred to as being "linked" or "in linkage". As used herein the term "close physical proximity" means that the two markers/alleles in question are close enough for linkage disequilibrium to be likely to arise.

Preferably the polymorphism(s) in linkage disequilibrium (and therefore the allele(s) in linkage) are separated from the p2 1E2c31 polymorphism and/or the p21E3+20 C/T polymorphism by a genetic linkage distance of less than 10 cM, or less than 9 cM, or less than 8 cM, or less than 7 cM, or less than 6 cM, or less than 5 cM, or less than 4 cM, or less than 3 cM, or less than 2 cM, or less than 1 cM.

Preferably the allele(s) in linkage exhibit a lod score of 2 or more, more preferably 3 or more with the p21E2c31 A allele and/or the p21E3+20 T allele.

Preferably the alleles/polymorphisms in "close physical proximity" are separated from the p21E2c31 polymorphism and/or the p21E3+20 C/T polymorphism by a physical distance of less than 10 Mb, or less than 9 Mb, or less than 8 Mb, or less than 7 Mb, or less than 6 Mb, or less than 5 Mb, or less than 4 Mb, or less than 3 Mb, or less than 2 Mb, or less than 1 Mb.

Further polymorphisms in linkage disequilibrium with or close proximity to p21E2c31 and p21E3+20 may be identified by searching publicly accessible genomic database resources (e.g. those accessible via the website of the National Center for Biotechnological Information (NCBI), USA). New variants may also be identified by scanning of genomic DNA for the presence of mutations/allelic variants using one or more of the many techniques known in the art for detection of genetic variation. Suitable techniques include, for example, single strand conformation polymorphism analysis (SSCP), PCR-SSCP heteroduplex analysis (HA), denaturing gradient gel electrophoresis (DGGE), DNA sequencing, RNase cleavage, chemical cleavage of mismatch (CCM) etc. (see review by Schafer and Hawkins, Nature Biotechnology, Vol: 16, pp 33-39, 1998). Scanning for the presence of mutations/allelic variants is typically carried out on a sample of genomic DNA isolated from a human subject. Genomic DNA may be conveniently isolated from a whole blood sample using standard techniques well known in the art.

Associations between a given polymorphic variant and susceptibility to Alzheimer's disease may be confirmed by carrying out genetic association studies, for example family-based or case-control association studies. The disease association of particular polymorphic variants may also be determined by evaluating the relationship between genotype and expression of markers of cell cycle progression in the brain (see WO 02/073212).

Alzheimer's disease is a complex and multi-factorial condition. In any given individual the development of AD is likely to be associated with accumulation of genetic variation within a single gene, or across multiple genes, and the accumulated variants may have an additive effect. As described in the applicant's published International patent application WO 02/073212, essentially any genetic variation which has an adverse effect on the function of a cell cycle regulatory gene may potentially result in by-pass of the G1/S transition check point, and consequential AD pathology.

In view of the foregoing, it is within the scope of the invention to perform genotyping of the p21E2c31 and p21 E3+20 C/T polymorphisms in conjunction with genotyping of "other" polymorphisms that are markers of susceptibility/pre-disposition to Alzheimer's disease in the same human subject, for example as a "panel screen" of multiple genetic variants. The "other" variants for inclusion in such a panel screen may include (but are not limited to) further polymorphisms in p21, polymorphisms, polymorphisms in other cell-cycle regulatory genes, any other polymorphism known to be associated with Alzheimer's disease, whether or not such polymorphism(s) occur in p21 or any other cell cycle regulatory gene, and polymorphisms in linkage disequilibrium with any of the above. In a preferred embodiment, genotyping of multiple polymorphisms in a single patient sample may be carried out simultaneously, for example with the use of a microarray or "gene chip".

In the context of the invention, "genotyping" of any given polymorphic variant may advantageously comprise screening for the presence or absence in the genome of the subject of both the normal or wild type allele and the variant or mutant allele or may comprise screening for the presence or absence of either individual allele, it generally being possible to draw conclusions about the genotype of an individual at a polymorphic locus having two alternative allelic forms just by screening for one or other of the specific alleles.

In accordance with the invention, genotyping of polymorphic variants can be carried out using any suitable methodology known in the art and it is to be understood that the invention is in no way limited by the precise technique used to carry out the genotyping.

Known techniques which may be used for genotyping single nucleotide polymorphisms include ligation detection reaction (LDR; Day, D. J., Speiser, P. W., White, P. C. & Barany, F. Genomics 29, 152-62 (1995)), mass spectrometry, particularly matrix-assisted laser desorption/ionization time-of-flight mass spectrometry (MALDI-TOF-MS), single nucleotide primer extension and DNA chips or microarrays (see review by Schafer, A. J. and Hawkins, J. R. in Nature Biotechnology, Vol 16, pp 33-39 (1998)). The use of DNA chips or microarrays may enable simultaneous genotyping at many different polymorphic loci in a single individual or the simultaneous genotyping of a single polymorphic locus in multiple individuals. SNPs may also be scored by DNA sequencing.

In addition to the above, SNPs are commonly scored using PCR-based techniques, such as PCR-SSP using allele-specific primers (described by Bunce M, et al., Tissue Antigens, 1995; 50: 23-31). This method generally involves performing DNA amplification reactions using genomic DNA as the template and two different primer pairs, the first primer pair comprising an allele-specific primer which under appropriate conditions is capable of hybridizing selectively to the wild type allele and a non allele-specific primer which binds to a complementary sequence elsewhere within the gene in question, the second primer pair comprising an allele-specific primer which under appropriate conditions is capable of hybridising selectively to the variant allele and the same non allele-specific primer. Further suitable techniques for scoring SNPs include PCR ELISA and denaturing high performance liquid chromatography (DHPLC).

If the SNP results in the abolition or creation of a restriction site, genotyping can be carried out by performing PCR using non-allele specific primers spanning the polymorphic site and digesting the resultant PCR product using the appropriate restriction enzyme (also known as PCR-RFLP). Restriction fragment length polymorphisms, including those resulting from the presence of a single nucleotide polymorphism, may be scored by digesting genomic DNA with an appropriate enzyme then performing a Southern blot using a labelled probe corresponding to the polymorphic region (see Molecular Cloning: A Laboratory Manual, Sambrook, Fritsch and Maniatis, Cold Spring Harbor Laboratory, Cold Spring Harbor, N.Y.).

The known techniques for genotyping polymorphisms are of general applicability and it will be readily apparent to persons skilled in the art that many of the known techniques may be adapted for the scoring of single nucleotide polymorphisms in the p21 gene. In the case of p21E2c31 and p21E3+20 C/T, the preferred technique for genotyping subjects for these SNPs is PCR-RFLP, as described in the accompanying Example and in Facher et al. ibid. However, the invention is not intended to be limited to the use of this technique.

Genotyping is preferably carried out in vitro, and is most preferably performed on an isolated sample containing genomic DNA prepared from a suitable tissue sample obtained from the subject under test. Most commonly, genomic DNA is prepared from a sample of whole blood or brain tissue, according to standard procedures which are well known in the art. If genomic sequence data for the individual under test in the region containing the SNP is available, for example in a genomic sequence database as a result of a prior genomic sequencing exercise, then genotyping of the SNP may be accomplished by searching the available sequence data.

In the case of genetic variants which have a detectable effect on the mRNA transcripts transcribed from a given gene, for example variants which cause altered splicing or which affect transcript termination or which affect the level or mRNA expression, then as an alternative to detecting the presence of the variant at the genomic DNA level, the presence of the variant may be inferred by evaluating the mRNA expression pattern using any suitable technique. Similarly, in the case of genetic variants which have a detectable effect on the protein products encoded by a gene, for example variants which cause a change in primary amino acid sequence (such as p21E2c31), structure or properties of the encoded protein, the presence of the variant may be inferred by evaluating the sequence, structure or properties of the protein using any convenient technique.

The above-described screening methods may be used prognostically to identify individuals pre-disposed to Alzheimer's disease (AD) by virtue of their genetic make-up. The "pre-disposition to Alzheimer's disease" may be manifest as an increased risk of developing disease as compared to individuals who do not possess a variant allele (i.e. subjects who are homozygous for the corresponding normal allele(s) p21E2c31 "C", p21E3+20 "C"), or as an earlier age of disease onset as compared to individuals who do not possess a variant allele. In a particular embodiment the method may be used to screen asymptomatic individuals (i.e. individuals who do not exhibit significant symptoms of AD according to standard diagnostic criteria) in order to identify those "at risk" of developing AD, and/or those likely to exhibit an earlier age of onset of AD. In particular embodiments, the screens may be used to assess risk of developing Alzheimer's disease in male human subjects or to assess likely age of onset of Alzheimer's disease in female human subjects. The results of such screens may facilitate early intervention with therapeutic treatments, particularly prophylactic treatments aimed at preventing, reducing or delaying the clinical symptoms of Alzheimer's disease.

In further embodiments the screening methods may be used to screen patients who exhibit clinical symptoms of Alzheimer's disease, for example to assist in correct diagnosis of AD and/or to investigate the genetic basis of suspected or confirmed AD.

The invention will be further understood by reference to the following experimental examples, together with the accompanying Figures, in which:

EXAMPLES

Example 1

Genotyping of p21cip 1 Polymorphisms

Patient Population

The subjects tested were full participants in the Oxford Project to Investigate Memory and Ageing (OPTIMA). The yearly routine OPTIMA examination includes a physical examination, cognitive and neuropsychological testing. Drug intake and any intercurrent infections are recorded.

Materials and Methods

Exon 2 of p21 cip was amplified from genomic DNA (extracted from brain or blood) using primers 5'-CGGGATC-CGGCGCCATGTCAGAACCGGC-3' (SEQ ID NO: 1) and 5'-CCAGACAGGTCAGCCCTTGG-3' (SEQ ID NO: 2) (Facher, E. A., et al., Association between human cancer and two polymorphisms occurring together in the p21Waf1/Cip1 cyclin-dependent kinase inhibitor gene. Cancer, 1997. 79 (12): p. 2424-9). PCR amplification was carried out in a final volume of 50 μl using 1.25 units of Taq DNA polymerase, 1.5 mM $MgCl_2$, 0.1% Gelatine, 200 μM of each dNTP in PCR buffer (75 mM Tris-HCl, pH 8.8, 20 mM $(NH_4)_2SO_4$ and 0.01% Tween™). The hot start (95° C. for 5') was followed by 30 cycles of 95° C. 1 min, 65° C. 1 min, 72° C. 1 min. The exon 2 polymorphism was detected using restriction enzyme digestion with BsmA I.

Exon 3 of p21 Cip was amplified from genomic DNA (extracted from brain or blood) using 5'-CCCAGG-GAAGGGTGTCCTG-3' (SEQ ID NO: 3) and 5'-GGGCG-GCCAGGGTATGTAC-3' (SEQ ID NO: 4) primers. PCR amplification was carried out in a final volume of 50 μl using 1.25 units of Taq DNA polymerase, 1.5 mM $MgCl_2$, 0.1% Gelatine, 200 μM of each dNTP in PCR buffer (75 mM Tris-HCl, pH 8.8, 20 mM $(NH_4)_2SO_4$ and 0.01% Tween™). The hot start (95° C. for 5 min) was followed by 30 cycles of 95° C. 30 s, 52° C. 30 s, 72° C. 30 s. The intronic mutation near exon 3 was detected by restriction enzyme digestion using Pst I.

Results

Figure 1:
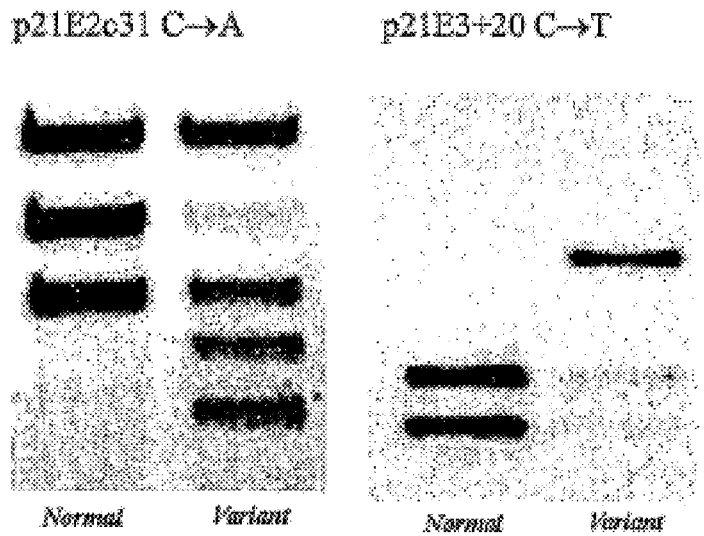
FIG. 1 illustrates genotyping of the p21E2c31 and p21E3+ 20 C/T polymorphisms of the human p2 1cip 1 gene by PCR-RFLP. Panel (a) shows genotyping of p21E2c31, exon 2 of p21 is amplified from genomic DNA by PCR as described in the accompanying examples, normal and variant alleles are then distinguished by digestion of the resulting PCR product with BsmA I. Panel (b) shows genotyping of the p21E3+20 C/T polymorphism, exon 3 of p21 is amplified from genomic DNA by PCR as described in the accompanying examples, normal and variant alleles are then distinguished by digestion of the resulting PCR product with Pst I.
Figure 2:
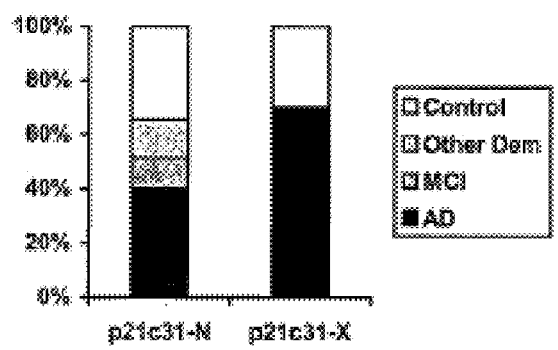
FIG. 2 illustrates the relationship between the p21 exon 2 codon 31 mutation (p21E2c31) and incidence of Alzheimer's disease. p21c31-N refers to the normal "C" allele; p21c31-X refers to the variant "A" allele.
Figure 2:
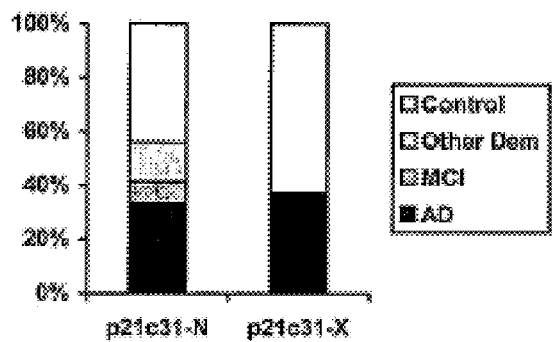
Figure 3:
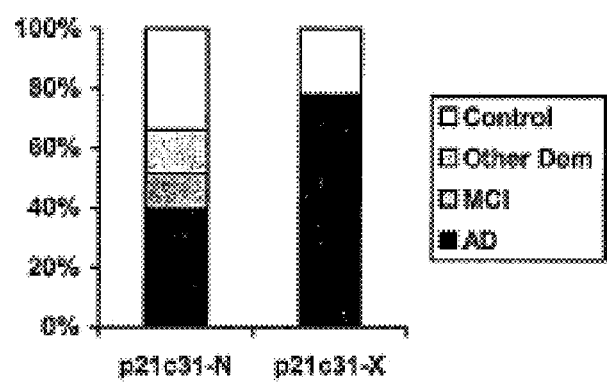
FIG. 3 illustrates the relationship between Alzheimer's disease and the co-occurrence of exonic (p21E2c31) and intronic (p21 E3+20 C/T) mutations of p21. p21c31-N refers to the normal individuals; p21c31-X refers to individuals having the variant "A" allele and the variant p21E3+ 20 "T" allele.
Figure 3:
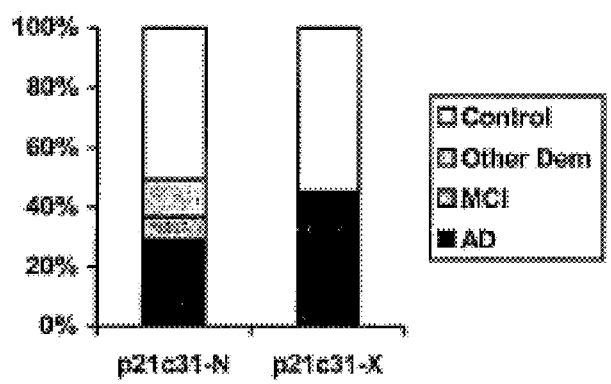
Figure 4:
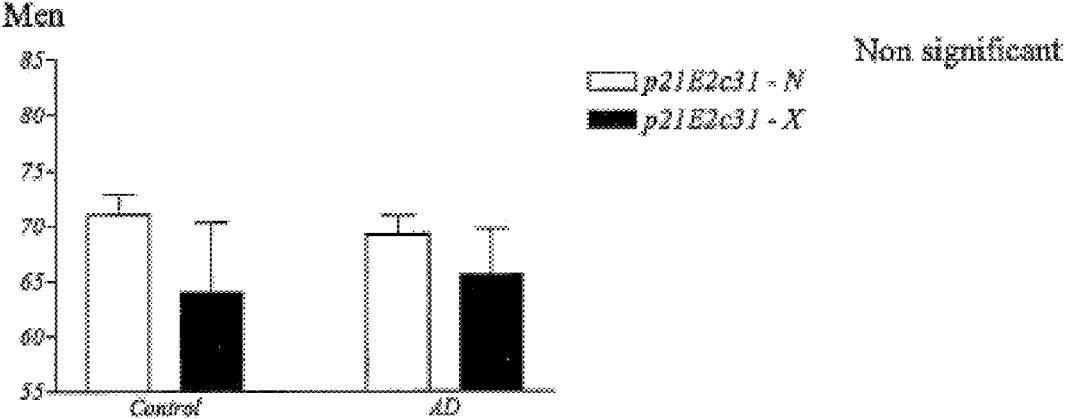
FIG. 4 illustrates the relationship between the p21 exon 2 codon 31 mutation (p21E2c31) and age of onset of Alzheimer's disease (years).
Figure 4:
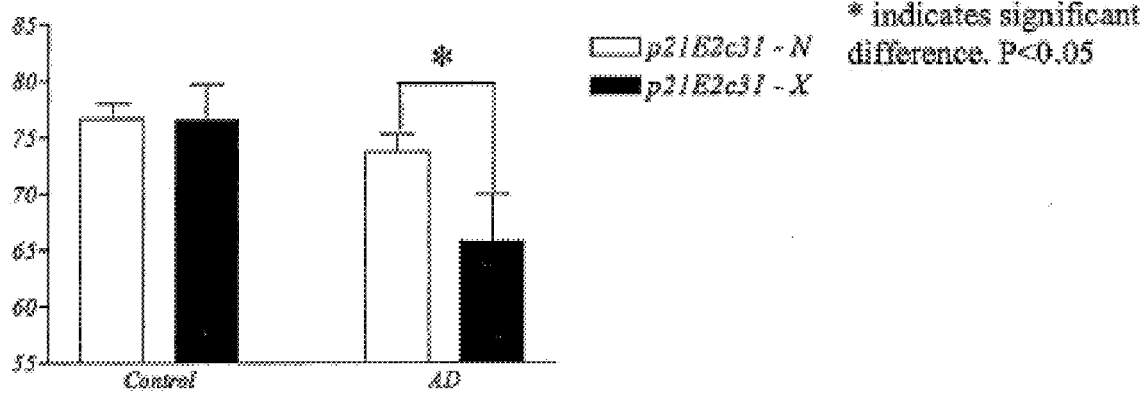

Results are illustrated in the accompanying FIGS. 1 to 4 and summarized in Table 1, below. The occurrence of the ser to arg mutation at codon 31 of p21cip 1 (i.e. the p21E2c31 C→A substitution) leads to an increased risk of Alzheimer's disease in men (FIG. 2). FIG. 3 illustrates that the significance of the association with Alzheimer's disease is increased where the p21E2c31 A allele and the p21E3+20 T allele occur together. In women, the risk of developing Alzheimer's disease was not significantly increased in this study population. However, the age of onset of Alzheimer's disease was significantly reduced in women carrying the variant allele.

TABLE 1

|  | | Gene Variant No. of Subjects | Gene Normal No. of Subjects | Relative Frequency | Odds Ratio |
|---|---|---|---|---|---|
| AD | | 12 | 76 | 14% | 1.61 |
| | Men | 7 | 41 | 15% | 4.44 |
| | Women | 5 | 35 | 13% | 0.98 |

TABLE 1-continued

|  |  | Gene Variant No. of Subjects | Gene Normal No. of Subjects | Relative Frequency | Odds Ratio |
|---|---|---|---|---|---|
| Controls |  | 10 | 82 | 11% |  |
|  | Men | 2 | 35 | 5% |  |
|  | Women | 8 | 47 | 15% |  |
| ODS |  | 1 | 30 | 3% |  |
|  | Men | 0 | 15 | 0% |  |
|  | Women | 1 | 15 | 6% |  |

CITED REFERENCES

1. Nagy, Z., M. M. Esiri, and A. D. Smith, The cell division cycle and the pathophysiology of Alzheimer's disease. Neuroscience, 1998. 84(4): p. 731-739.
2. Nagy, Z., et al., Cell cycle kinesis in lymphocytes in the diagnosis of Alzheimer's disease. Neurosci Lett, 2002. 317(2): p. 81-4.
3. Harima, Y., et al., Polymorphism of the WAFT gene is related to susceptibility to cervical cancer in Japanese women. Int J Mol Med. 2001. 7(3): p. 261-4.
4. Facher, E. A., et al., Association between human cancer and two polymorphisms occurring together in the p21Waf1/Cip1 cyclin-dependent kinase inhibitor gene. Cancer, 1997. 79(12): p. 2424-9.

What is claimed is:

1. A method for indicating the pre-disposition of a male human subject to developing Alzheimer's disease, which method comprises:
   (A) assaying a nucleic acid sample obtained from the subject for a p21 polymorphism to determine the allele present at said polymorphism, said p21 polymorphism being a p21 E2c31 C/A polymorphism;
   and
   (B) correlating the allele present at said polymorphism with the pre-disposition of said subject to developing Alzheimer's disease;
   wherein a determination that said subject possesses a variant A allele of said p21E2c31 C/A polymorphism is taken as an indication that the subject is pre-disposed to Alzheimer's disease.

```
                         SEQUENCE LISTING

<160> NUMBER OF SEQ ID NOS: 4

<210> SEQ ID NO 1
<211> LENGTH: 28
<212> TYPE: DNA
<213> ORGANISM: Homo sapiens

<400> SEQUENCE: 1
cgggatccgg cgccatgtca gaaccggc                                       28

<210> SEQ ID NO 2
<211> LENGTH: 20
<212> TYPE: DNA
<213> ORGANISM: Homo sapiens

<400> SEQUENCE: 2
ccagacaggt cagcccttgg                                                20

<210> SEQ ID NO 3
<211> LENGTH: 19
<212> TYPE: DNA
<213> ORGANISM: Homo sapiens

<400> SEQUENCE: 3
cccagggaag ggtgtcctg                                                 19

<210> SEQ ID NO 4
<211> LENGTH: 19
<212> TYPE: DNA
<213> ORGANISM: Homo sapiens

<400> SEQUENCE: 4
gggcggccag ggtatgtac                                                 19
```

2. A method for diagnosing Alzheimer's disease in a male human subject exhibiting clinical symptoms of Alzheimer's disease, which method comprises:
(A) assaying a nucleic acid sample obtained from the subject for a p21 polymorphism to determine the allele present at said polymorphism, said p21 polymorphism being a p21 E2c31 C/A polymorphism; and
(B) correlating the allele present at said polymorphism with the diagnosis of Alzheimer's disease in said subject;
wherein a determination that said subject possesses a variant A allele of said p21E2c31 C/A polymorphism is diagnostic that said subject has Alzheimer's disease.

3. A method of determining the existence of a genetic basis for Alzheimer's disease in a male human subject, which method comprises:
(A) assaying a nucleic acid sample obtained from the subject for a p21 polymorphism to determine the allele present at said polymorphism, said p21 polymorphism being a p21 E2c31 C/A polymorphism; and
(B) correlating the allele present at said polymorphism with its contribution to the genetic basis for Alzheimer's disease in said subject;
wherein a determination that said subject possesses a variant A allele of said p21E2c31 C/A polymorphism indicates that a genetic variation that contributes to the genetic basis for Alzheimer's disease is present in said subject.

4. The method of claim 1, wherein said assaying comprises a ligation detection reaction, single nucleotide primer extension, DNA sequencing or mass spectroscopy.

5. The method of claim 2, wherein said assaying comprises a ligation detection reaction, single nucleotide primer extension, DNA sequencing or mass spectroscopy.

6. The method of claim 3, wherein said assaying comprises a ligation detection reaction, single nucleotide primer extension, DNA sequencing or mass spectroscopy.

7. A method of determining the existence of a genetic basis for earlier onset of Alzheimer's disease in a female human subject exhibiting clinical symptoms of Alzheimer's disease, which method comprises:
(A) assaying a nucleic acid sample obtained from the subject for a p21E2c31 C/A polymorphism to determine the allele present at said polymorphism, and
(B) correlating the allele present at said polymorphism with the existence of a genetic basis for earlier onset of Alzheimer's disease in said subject, wherein a determination that said subject possesses a variant A allele of said p21E2c31 C/A polymorphism indicates that a genetic variation that contributes to the genetic basis for earlier onset of Alzheimer's disease is present in said subject, wherein said assaying comprises a ligation detection reaction, single nucleotide primer extension, DNA sequencing or mass spectroscopy.

8. The method of claim 1, wherein said assaying employs a DNA microarray.

9. The method of claim 2, wherein said assaying employs a DNA microarray.

10. The method of claim 3, wherein said assaying employs a DNA microarray.

11. The method of claim 7, wherein said assaying employs a DNA microarray.

12. The method of claim 1, wherein said method further comprises determining whether said male human subject possesses the variant T allele of the p21E3+20 C/T polymorphism in the p21cip1 gene, wherein the presence of said variant T allele of said p21E3+20 C/T polymorphism is further indicative that said subject is pre-disposed to Alzheimer's disease.

13. The method of claim 2, wherein said method further comprises determining whether said male human subject possesses the variant T allele of the p21E3+20 C/T polymorphism in the p21cip1 gene, wherein the presence of said variant T allele of said p21E3+20 C/T polymorphism is further diagnostic that said subject has Alzheimer's disease.

14. The method of claim 3, wherein said method further comprises determining whether said male human subject possesses the variant T allele of the p21E3+20 C/T polymorphism in the p21cip1 gene, wherein the presence of said variant T allele of said p21E3+20 C/T polymorphism is further indicative that a genetic variation that contributes to the genetic basis for Alzheimer's disease is present in said subject.

* * * * *